United States Patent [19] [11] 3,955,890
Bessis et al. [45] May 11, 1976

[54] METHOD OF MEASURING THE DEFORMATION CAPACITY OF MICROSCOPIC OBJECTS, MORE PARTICULARLY RED BLOOD CORPUSCLES AND A DEVICE FOR IMPLEMENTING THE METHOD

[75] Inventors: Marcel Bessis; Narla Mohandas, both of Paris, France

[73] Assignee: Institut National de la Sante et de la Recherche Medicale Organisme D'Etat, Paris, France

[22] Filed: Apr. 29, 1975

[21] Appl. No.: 572,876

[30] Foreign Application Priority Data
May 10, 1974 France.............................. 74.16160

[52] U.S. Cl................................. 356/39; 356/102; 356/103; 356/197
[51] Int. Cl.².......................................... G01N 11/00
[58] Field of Search............. 356/39, 102, 103, 104, 356/196, 197

[56] References Cited
UNITED STATES PATENTS
3,662,176  5/1972  Kamentsky et al................. 356/104
3,770,349  11/1973  Legoretta-Sanchez............. 356/102
3,873,204  3/1975  Friedman et al...................... 356/39

Primary Examiner—John K. Corbin
Assistant Examiner—Richard A. Rosenberger
Attorney, Agent, or Firm—Browdy and Neimark

[57] ABSTRACT

A method and device for measuring the deformation capacity of microscopic objects, more particularly, red blood corpuscles includes an enclosure comprising two mobile, coaxial, cylindrical walls which can rotate relative to one another. The objects to be measured are put into a liquid suspension and then placed between the two walls. An optical system directs a beam of light through the suspension and the diffraction characteristics of the undeformed objects may be observed and recorded. The cylindrical walls are then driven at different rotational speeds with respect to their common axis, and the diffraction characteristics of the deformed objects are observed and recorded. The deformation of the microscopic objects can be determined as a function of the relative speed of the walls by comparing the diffraction characteristics of the objects in their undeformed and deformed states.

10 Claims, 1 Drawing Figure

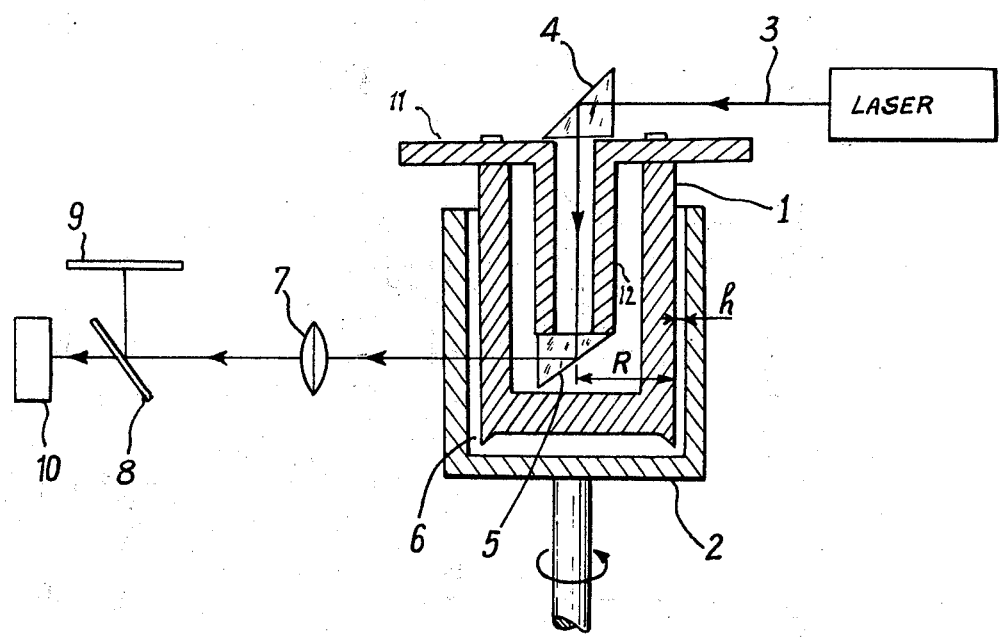

METHOD OF MEASURING THE DEFORMATION CAPACITY OF MICROSCOPIC OBJECTS, MORE PARTICULARLY RED BLOOD CORPUSCLES AND A DEVICE FOR IMPLEMENTING THE METHOD

BACKGROUND OF THE INVENTION

1. Field of the Invention

The present invention relates to a method of measuring the deformation capacity(deformability)of microscopic objects, more particularly, of living cells such as red blood corpuscles.

2. Description of the Prior Art

It is known that the deformation capacity of red blood corpuscles plays an essential role in their functions and their time of survival. It is this capacity which enables these generally discocytic cells having a diameter on the order of 8 microns to pass through the capillary vessels having a diameter on the order of 2 to 3 microns.

Numerous methods of measuring the deformation capacity of red blood corpuscles have been proposed. In particular, it is possible to cite measurement of the relative negative pressure required to suck a portion of the cell into a micropipette, measurement of the elongation of the cells adhering to a surface under the action of a liquid flow or measurement of the time required for a specific quantity of cells to pass through a filter having calibrated microscopic pores.

All these methods, with the exception of the second method have the disadvantage that the forces acting on the cells are not well defined. In the case of the second method, the deformation of the cells depends partly on the manner in which they adhere to the surface. In addition, it is necessary to measure the elongation cell by cell. Accordingly, considerable time is required to obtain statistical data on a large number of cells.

Another known method of studying the deformation of red blood corpuscles consists in placing a sample of liquid containing these corpuscles in suspension between two coaxial walls driven at different speeds of rotation with respect to their common axis in the manner of the walls of a rotary viscometer having coaxial cylinders. This method makes it possible to accurately determine the fluid stresses which are exerted on the corpuscles by virtue of the gradient of the rotational speed. However, even with this method, the deformation of each cell must be measured individually after fixing the cells in the deformed state and examining them under a microscope. Accordingly, a considerable amount of time is required for this operation.

Lastly, it is also known that the average dimensions of very small objects such as specks of dust or droplets can be measured by an optical diffraction method. This method has also been used to determine the average diameter of red blood corpuscles, but it has not been employed to measure cell deformability under dynamic conditions.

It has been found that if a group of microscopic objects which initially are spatially distributed in an arbitrary manner, become aligned, change their shape and dimensions under the action of applied forces, the diffraction patterns which are obtained reflect these changes in shape and dimensions. If the sample under examination contains a mixture of different particle types the patterns obtained represent a combination of the patterns which would be produced by each of the individual types.

SUMMARY OF THE INVENTION

The object of the present invention is to enable the deformation capacity of a group of microscopic objects to be measured continuously in a simple and accurate manner by combining the method of measuring deformation by means of the gradient of the rotational speed and the diffraction method.

According to the invention the method of measuring the deformation capacity of microscopic objects, more particularly, of living cells such as red blood corpuscles in suspension in a liquid, wherein this liquid is placed between two coaxial walls and wherein these walls are driven at different rotational speeds with respect to their common axis is characterized in that a light beam is passed through this liquid substantially normal to the common axis, and that the diffraction pattern produced by the microscopic objects is observed and in that the characteristic dimensions of the diffraction rings are measured as a function of the differential speed of the two walls.

In this way it is possible to obtain accurate measurements of the deformation capacity of the objects under examination in a simple and continuous manner. In addition, as the measurement obtained is a statistical measurement, it immediately provides the average value of a large number of objects. If the sample being studied contains a mixture of groups of objects having different features, this fact is immediately visible in the appearance of the diffraction pattern and the features of each of the groups can be rapidly ascertained.

The device according to the invention for implementing the above method is characterized in that it comprises an enclosure comprising two mobile, coaxial, cylindrical walls rotating with respect to each other, means for driving these walls at different rotational speeds with respect to their common axis, a light source, means or forming from this source a parallel light beam directed substantially normal to the common axis and means for observing and/or recording the pattern of diffraction ad infinitum formed by the microscopic objects.

Other objects, features and advantages of the present invention will be made apparent in the following detailed description of a preferred embodiment provided with reference to the accompanying non-limitative drawings.

BRIEF DESCRIPTION OF THE DRAWING

The single FIGURE is a diagrammatic, vertical sectional view of a device for implementing the method according to the invention.

DESCRIPTION OF THE PREFERRED EMBODIMENT

The device represented in the drawing comprises a mechanical part designed to subject the microscopic objects to be studied to well defined forces which can be accurately measured and an optical part for indicating and measuring the deformation of these objects under the action of these forces.

The mechanical part comprises an enclosure defined by an inner cylinder 1 and an outer cylinder 2 which are coaxially disposed. The lateral walls of these cylinders are transparent.

In the embodiment represented, the inner cylinder 1 is stationary. Means which are known per se and which are not represented enable the outer cylinder 2 to be rotated about the common axis of the two cylinders at predetermined regulatable speeds. However, it is also possible, without departing from the scope of the invention, for these two cylinders to be rotated about their common axis at different speeds relative to a fixed support.

By way of example, the inner cylinder may have an outer radius R on the order of 25 mm.

The annular space 6 defined by the inner and outer lateral walls of the cylinders 1 and 2 has a radial thickness $h$ of less than one millimeter, preferably of 0.3–0.5 mm.

The optical measuring system comprises a light source. In the embodiment represented this source is a laser capable of emitting a narrow parallel light beam 3 which is represented substantially normal to the common axis of the cylinders 1 and 2.

An optical system is provided for directing the light beam at right angles to the two coaxial lateral walls of the two cylinders in such a way that it crosses the annular space 6 in a radial direction. For example, this system may comprise two reflecting prisms 4 and 5 attached to a support 11 which is itself carried by the inner cylinder 1. The support 11 comprises a cylindrical part 12 which is coaxial to the cylinders 1 and 2 which acts as a guide for the light beam 3 in its path parallel to the axis.

Lastly, the optical system comprises an observation device which is disposed outside of the cylinders and which comprises, for example a convergent lens 7. The sensitive plate of a photo camera or recorder 10 is disposed in the image focal plane of the lens 7. A retractable reflector 8 enables the emergent beam to be directed onto an observation screen 9. This device makes it possible to obtain at a finite distance the image of diffraction ad infinitum produced by the microscopic objects illuminated with parallel light.

The method according to the invention will now be described in conjunction with the modus operandi of the device represented. To simplify matters it will be assumed that the microscopic objects to be studied are red blood corpuscles.

The blood sample containing the corpuscles in suspension is placed in the annular space 6. A small quantity of solution is required, for example, on the order of 4ml. To avoid having to employ excessively high rotational speeds, a specific amount of inert macromolecules such as dextran is added to the sample to increase its viscosity. The suspending solution is isotonic and has a pH of 7.4.

The laser is then put into operation and the diffraction image obtained is observed on the screen 9. At this point the two cylinders 1 and 2 are immobile. In the great majority of cases this image consists of concentric circular rings which are alternately dark and bright and which surround a bright, central, circular spot. The diameter of the first dark ring is measured.

The outer cylinder 2 is then driven in rotation at a predetermined speed. In the simplest case where the sample comprises a single group of individual objects it is noted that the rings have an elliptical form and it is possible to measure the large and small axes of this form. This elliptical form is a result of the deformation of the red blood corpuscles into substantially elliptical forms under the action of the stresses exerted on the corpuscles by the liquid.

The elliptical form is increasingly stretched-narrowed as the speed of rotation of the outer cylinder 2 increases. When the latter is returned to the rest state the diffraction pattern reassumes a circular form.

To obtain a number representative of the dynamic deformation capacity of the corpuscles it is necessary to proceed as follows :

On one hand, it is necessary to calculate for each rotational speed the tangential stress T, exerted by the liquid on the corpuscles by virtue of its viscosity and the velocity gradient in the radial direction using the formula :

$$T = \mu \ \frac{2 \pi NR}{60 h}$$

in which $\mu$ is the viscosity of the liquid and N the number of rotations per minute of the outer cylinder 2.

This formula applied to the simple case described above where the inner cylinder 1 remains immobile. In the more general case in which the outer and inner cylinders having the radii $R_1$ AND $R_2$ are driven in rotation at the respective number of rotations per minute of $N_1$ and $N_2$ the formula to apply would be the following :

$$T = \mu \ \frac{2 \pi}{60} \ \frac{N_1 R_1 - N_2 R_2}{h}$$

On the other hand, the dimensions of the deformed corpuscles is obtained in the following manner :

The diameter $d_0$ of the non-deformed corpuscles is provided by the known formula :

$$d_0 = \frac{1.22 \lambda f}{a_0}$$

in which $\lambda$ is the wave length of the light employed, $a_0$ is the diameter of the first dark ring and $f$ is the foxal distance of the lens 7.

It is possible to characterize the elliptically deformed corpuscles by the dimensions of one of their axes, for example, the major axis $d_n$ which is linked to the minor axis dimension $a_n$ of the first elliptical diffraction ring by a similar formuls to the preceding one. The following deformation is thus obtained :

$$\frac{d_n}{d_0} = \frac{a_0}{a_n}$$

The deformation capacity of the corpuscles can be measured by correlating the increase in major axis dimension with the applied shear stresses. Thus, this method makes it possible to very rapidly determine the variations in the deformation capacity as a function of the stress applied.

If the sample contains a plurality of separate groups, for example a first group of deformable individual objects and a second group of virtually non-deformable individual objects, then an elliptical diffraction pattern given by the deformable group will be super-imposed on the circular pattern given by the undeformable group, in the dynamic state. Thus, in this way, it is not only possible to detect a mixture of groups but it is also possible to measure the deformation capacity of each of the groups by the method described above.

The present invention is obviously not limited to the embodiment described and numerous modifications can be made thereto without departing from the scope of the invention. For example, it is possible to use two laser beams having different wave lengths to obtain colored diffraction rings and thus facilitate the measuring operation. The laser source may be replaced by a punctiform light source having a paralleling device in series therewith. It is also possible to replace the prisms 4 and 5 by reflectors. Other geometrical arrangements of the viscometer giving similar shear stresses can also be used.

What is cliamed is :

1. A method of measuring the deformation and deformation capacity of microscopic objects in suspension in a liquid comprising the steps of :
  placing said suspension between inner and outer transparent coaxial walls having a common axis of rotation ;
  directing a beam of light through said liquid substantially normal to the common axis of said coaxial walls causing diffraction rings to form on a screen;
  measuring the characteristic dimensions of the diffraction rings while said walls are at rest ;
  rotating said inner and outer coaxial walls at different speeds of rotation relative to their common axis of rotation ;
  measuring the characteristic dimensions of the diffraction rings while said walls are rotating relative to each other ; and
  determining the deformation and the deformation capacity of said microscopic objects as a function of the relative speed of rotation of the two walls.

2. A method as claimed in claim 1 wherein an inert macromolecule such as dextran is added to said suspension to increase its viscosity.

3. A method as claimed in claim 1 wherein said microscopic objects are red blood corpuscles.

4. A method as claimed in claim 1 wherein said inner wall is immobile when said outer wall is rotating.

5. A device implementing the method according to claim 1 comprising :
  an outer cylindrical wall ;
  an inner cylindrical wall disposed with said outer cylindrical wall, and coaxial with said outer wall, the distance between walls forming an annular space ;
  rotating means connected to said outer and inner cylindrical walls for driving said walls at different rotational speeds with respect to their common axis;
  a light source disposed adjacent to said outer and inner walls ;
  directing means connected to one of said walls for directing the light beams from said light source through said suspension in a parallel light beam substantially normal to the common axis of said walls; and
  imaging means adjacent to said walls for observing the pattern of diffraction of said light beam after if passes through said suspension.

6. A device according to claim 5 further including recording means for recording the diffraction pattern of said microscopic objects.

7. A device according to claim 5 wherein the radial thickness of said annular space is ≤ 1 mm.

8. A device according to claim 5 wherein said light source is a laser.

9. A device according to claim 5 wherein said microscopic objects are red blood corpuscles.

10. A device according to claim 5 wherein said walls are transparent.

* * * * *